United States Patent
Liu et al.

(10) Patent No.: US 9,144,707 B2
(45) Date of Patent: Sep. 29, 2015

(54) EXERCISERS WITH SMART MANAGE SYSTEM AND METHODS USING THE SAME

(71) Applicant: FOOTWEAR & RECREATION TECHNOLOGY RESEARCH INSTITUTE, Taichung (TW)

(72) Inventors: Pao-Pao Liu, Taichung (TW); David Lai, Taichung (TW); Chiu-Chieh Chen, Taichung (TW); Ching-Yu Chuang, Taichung (TW); Chung-Kai Huang, Taichung (TW)

(73) Assignee: FOOTWEAR & RECREATION TECHNOLOGY RESEARCH INSTITUTE, Taichung (TW)

( * ) Notice: Subject to any disclaimer, the term of this patent is extended or adjusted under 35 U.S.C. 154(b) by 233 days.

(21) Appl. No.: 13/956,889

(22) Filed: Aug. 1, 2013

(65) Prior Publication Data

US 2014/0113769 A1    Apr. 24, 2014

(30) Foreign Application Priority Data

Oct. 18, 2012    (TW) .............................. 101138480 A (51) Int. Cl.
| | |
|---|---|
| A63B 71/00 | (2006.01) |
| A63B 22/06 | (2006.01) |
| A63B 22/02 | (2006.01) |
| A63B 22/04 | (2006.01) |
| G06Q 50/22 | (2012.01) |

(52) U.S. Cl.
CPC .................. *A63B 22/06* (2013.01); *A63B 22/02* (2013.01); *A63B 22/04* (2013.01); *G06Q 50/22* (2013.01)

(58) Field of Classification Search
CPC ........ A63B 22/06; A63B 22/02; A63B 22/04; G06Q 50/22
IPC ......................................................... A63B 24/00
See application file for complete search history.

(56) References Cited

U.S. PATENT DOCUMENTS

| 7,507,183 B2* | 3/2009 | Anderson et al. .................. 482/1 |
| 7,699,755 B2* | 4/2010 | Feldman et al. .................. 482/8 |
| 8,341,557 B2* | 12/2012 | Pisula et al. .................. 715/863 |
| 2004/0171464 A1* | 9/2004 | Ashby et al. .................. 482/54 |
| 2004/0198555 A1* | 10/2004 | Anderson et al. .................. 482/8 |
| 2009/0221880 A1* | 9/2009 | Soderberg et al. ............ 600/300 |
| 2010/0324380 A1* | 12/2010 | Perkins et al. ................. 600/301 |
| 2013/0102440 A1* | 4/2013 | Hutchins et al. .................. 482/8 |

* cited by examiner

*Primary Examiner* — Glenn Richman
(74) *Attorney, Agent, or Firm* — WPAT, P.C.; Anthony King (57) ABSTRACT

The present invention relates to exercisers having information management system comprising a main frame of the exerciser, a measuring module, a signal processing module and an identifier generating module. The measuring module measures the movement of the exerciser and/or the physical status of the user and collects signals from the equipment and/or user. The signal processing module processes the signals received and then generates fitness information and/or physical information. The identifier generating module converts the information into an identifier and displays on a monitor. The user can easily obtain the identifier by using mobile devices, without printing, for him or her to save, manage and utilize the information.

9 Claims, 8 Drawing Sheets

EXERCISERS WITH SMART MANAGE SYSTEM AND METHODS USING THE SAME

FIELD OF THE INVENTION

The present invention relates to exercisers with smart manage system and methods using the same, particularly to a fitness training technique having information management system that is applicable to rehabilitation, fitness and so on.

BACKGROUND OF THE INVENTION

Current prior arts are designed for users to exercise, control weight and build body strength, such as a cycling equipment, a treadmill, an elliptical, a strength equipment, a row and a DDR (Dance Dance Revolution). A specific exercise mode must be designed for individual needs in order to maximize the efficiency of rehabilitation or fitness and to effectively avoid injury or danger. Therefore, fitness information management appears to be important. The fitness information management system manages not only every exercise status of users but also their body conditions to monitor if they have gotten enough and proper exercise. Users' recipes for next exercise will be generated based on the integrated information system. To effectively manage the fitness information is very helpful to meet individual exercise needs.

Current fitness information management of exercisers is mainly to retrieve information from equipments and then store in a computer as users' or trainers' reference to make exercise recipes for specific goals. The fitness information management system of current prior arts requires computers to process all information, but its high cost is too expensive to apply to personal exercisers used at home for a user to manage his or her fitness information. Each fitness center might have computers to monitor the system, but it is inconvenient for individuals to retrieve fitness information from the computers by their own for further analysis of their fitness status at home. Inasmuch as to return to the fitness center is the only way to obtain their personal data, it is an obvious disadvantage and inflexibility of the system to limit the management of the fitness information.

A prior art of fitness training technique disclosed in R.O.C. Patent Application No. I350522 is to enter personal information such as age, gender, height, weight, body flexibility, physical fitness, muscular power, aerobic capacity, favorable sports and so on to generate a personal database, and then a personal exercise recipe can be obtained from its predefined neural network models. Another prior art disclosed in R.O.C. Patent Application No. M374335 measures a user's height, weight, seated forward bending length, times of sit-ups per minute, distance of standing long jump and fixed distance running record to define the user's physical fitness level for creating a proper exercise recipe. These prior arts lack a better mechanism to manage fitness information.

In order to improve above disadvantages of the prior arts, an application of barcodes has been designed to manage fitness information as disclosed in R.O.C. Patent Application No. I336618, entitled "Application of fitness management device to simultaneously detect biological certification and arrhythmia". It stores a user's registered module, characteristics and doctor's prescriptions in a two-dimensional bar-coded pattern. When the user logs in, the system will verify the instantaneous electrocardiogram against the registered module. In this application, the system will monitor and judge if fatal arrhythmia is going to happen to the user or not, and will automatically decide if it needs to send out an emergency call. It will also calculate required amount of exercise and prompt warning based upon the exercise recipe prescribed by the doctor. Hence, the goal of personal fitness management can be simply achieved.

A managing device of an exercising entity disclosed in R.O.C. Patent Application No. 200910231 entitled "Physical activity manager" and issued as U.S. Pat. No. 7,914,419, encapsulates a user's exercise information into an identifier such as a two-dimensional bar-code which can be processed, e.g. scanning, through a plurality of devices like a mobile phone or a PDA (Personal Digital Assistant). This device is designed to plan, monitor and record the capability of an exercising entity. Its planning feature allows a user or fitness professional to set exercise or activity regulations for the entity in advance, its monitoring feature supports tracking of instantaneous physical fitness or activity of the entity, and its recording feature enables the user to save information in the user's database for further evaluation of health or physical fitness.

Both above prior arts apply two-dimensional barcodes for recording users' personal fitness information, but the identifiers must be printed on paper for data retrieval by scanning. It is impossible for a user to print out the barcode and utilize the information without a printer and a bar-code reader at home. Even in a fitness center, it is inconvenient for a user to retrieve required information from the system or equipment provided by the fitness center. Furthermore, the identifier generator does not directly link to the signal process unit of the exerciser, but the identifier must be generated and retrieved via the computer system of the fitness center. Not only is the utilization of the identifier limited, but it is extremely inconvenient for the user.

SUMMARY OF THE INVENTION

The first object of the present invention is to provide a simplified mechanism, an information management system of exercisers (exercising equipment), which is easy to use for information management and applicable to various electronic devices. It comprises a main frame of the exerciser, a measuring module, a signal processing module and an identifier generating module. The measuring module measures the movement of the exerciser and/or the physical status of the user and collects signals from the equipment and/or user. The signal processing module processes the signals received and then generates fitness information and/or physical information. The identifier generating module converts the information into an identifier (e.g. barcode) and displays on a monitor. The user can easily obtain the identifier by using mobile devices, without printing, for him or her to save, manage and utilize the information.

The second object of the present invention is to provide a simplified mechanism, an information management system of exercisers (exercising equipment), which is easy and available for all users to use for information management and is applicable to various electronic devices. It comprises the same elements as depicted in the first object but the identifier generating module is allocated on the main frame. Therefore, the identifier can be generated from the main frame at the user end.

The third object of the present invention is to provide a simplified mechanism, an information management system of exercisers (exercising equipment), which is easy and available for all users to retrieve identifiers (barcodes) and to use for information management and is applicable to various electronic devices. It comprises the same elements as depicted in the first object but the identifier generating module and the monitor are allocated on the main frame. Therefore, the identifier can be generated and promptly displayed on the monitor from the main frame at the user end.

The fourth object of the present invention is to provide a simplified mechanism, an information management system of exercisers (exercising equipment), which is easy and available for all users to promptly and directly retrieve or manage the information and is applicable to various electronic devices. It comprises the same elements as depicted in the first object but the identifier generating module is built in the signal processing module on the main frame. Therefore, the fitness or physical information can be promptly and directly retrieved and the identifier can be generated and displayed from the main frame at the user end.

The fifth object of the present invention is to provide a simplified mechanism, an information management system of exercisers (exercising equipment), which is convenient for users to retrieve, save and manage the information and is applicable to various electronic devices. It comprises the same elements as depicted in the first object but the identifier generating module is employed to generate and display two-dimensional barcodes as identifiers for the user to easily save and utilize the identifiers.

The sixth object of the present invention is to provide a simplified mechanism, an information management system of exercisers (exercising equipment), which is convenient for users to encode and personally manage the information and is applicable to various electronic devices. It comprises the same elements as depicted in the first object, but also includes a user's ID identifying module and a securing module built in the identifier generating module. The user's ID identifying module receives and identifies the user's personal information and then decides proper exercise for the user to operate the fitness equipment, and the securing module encodes and secures the user's personal information into the identifier (barcode).

DETAILED DESCRIPTION OF THE PREFERRED EMBODIMENT

I. The First Embodiment of the Present Invention

Figure 1:
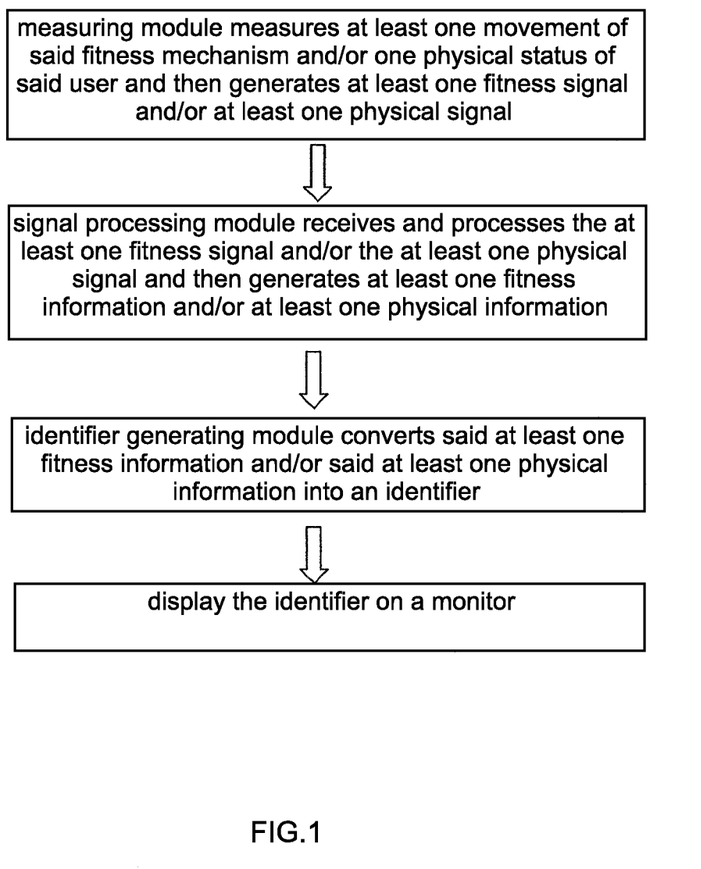
FIG. 1 is a method flow chart of the present invention.
Figure 2:
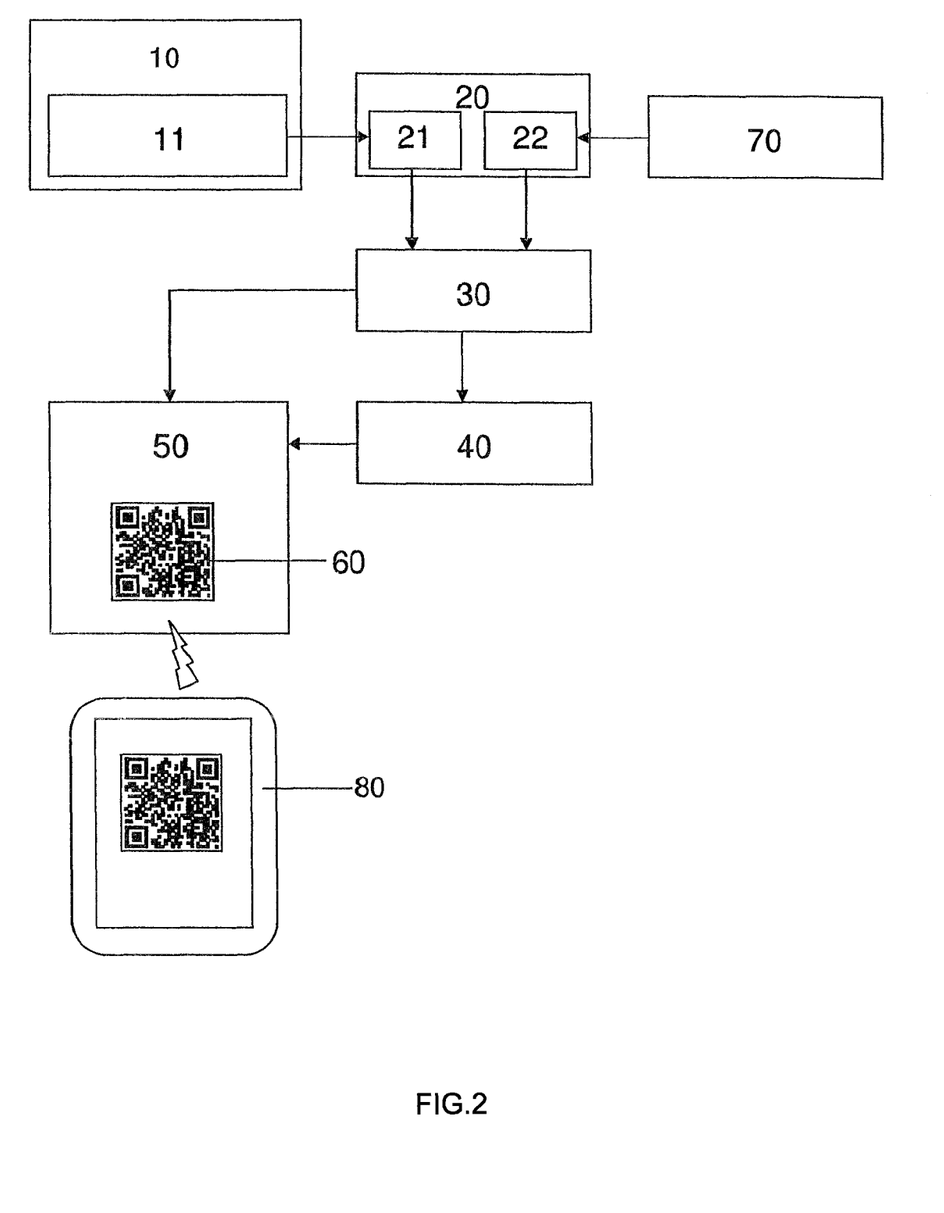
FIG. 2 is a systematic flow chart of the first embodiment in accordance with the present invention.
Figure 7:
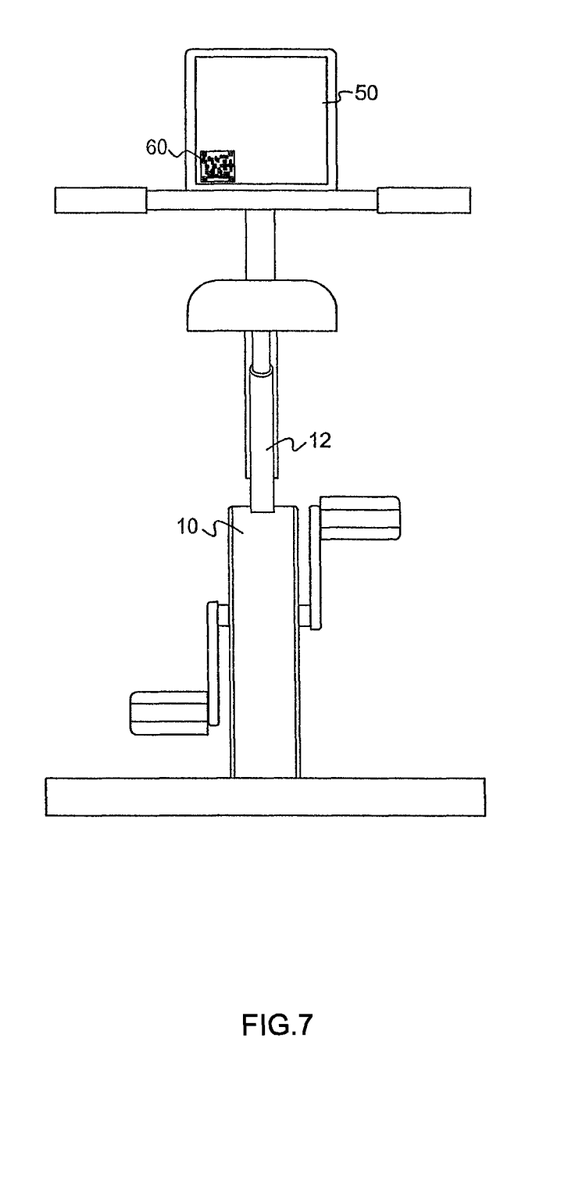
FIG. 7 is an application drawing of a cycling equipment in accordance with the present invention.
Figure 8:
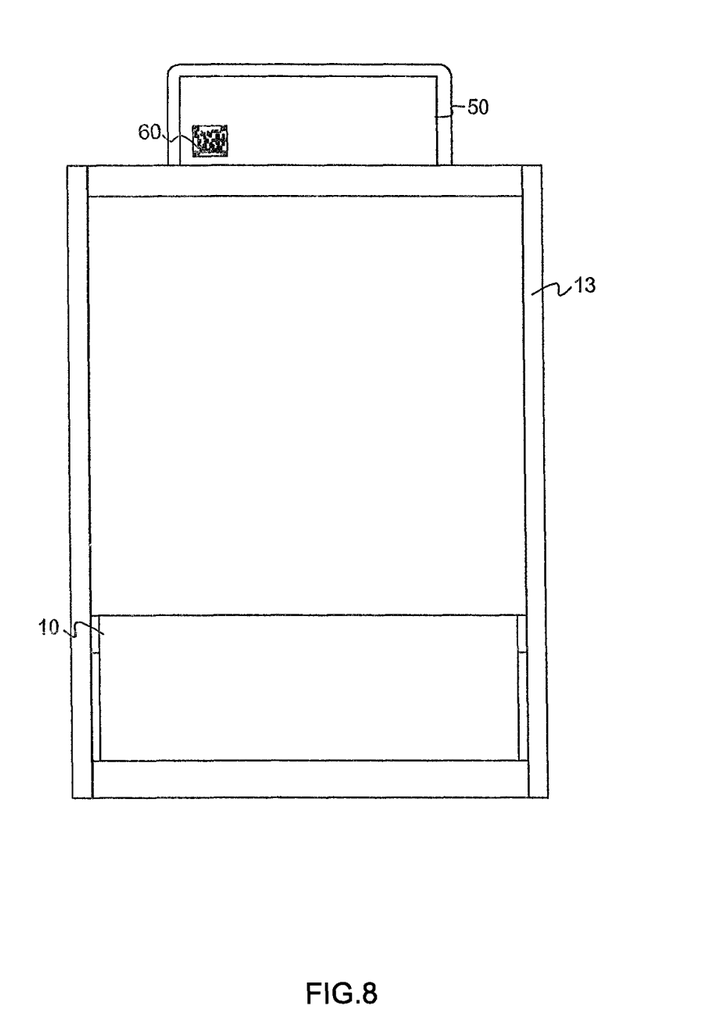
FIG. 8 is an application drawing of a treadmill in accordance with the present invention.

Referring to FIGS. 1 and 2, it is an embodiment to achieve the first object of the present invention. The system comprises a main frame 10 of the exerciser, a measuring module 20, a signal processing module 30 and an identifier generating module 40. The exerciser could be a cycling equipment, a treadmill, an elliptical equipment, a weight lifting equipment, a body-building equipment or a rehabilitation equipment. The application of the cycling equipment 12 is shown as in FIG. 7 and the application of the treadmill 13 is shown as in FIG. 8. The fitness mechanism 11 of the main frame 10 allows a user 70 to do exercise and activate functions of the system. The processing steps are depicted as below. First of all, the measuring module 20 measures the movement of the fitness mechanism 11 and/or the physical status of the user and then generates fitness signals and/or physical signals. Secondly, the signal processing module 30 receives and processes the fitness signals and/or physical signals and then generates fitness information and/or physical information. After the user finishes the exercise, the identifier generating module 40 converts the fitness information and/or physical information into an identifier (barcode) 60 which will be displayed on the monitor 50. Wherever the monitor 50 is located, the identifier (barcode) 60 is going to be displayed on the monitor 50. Therefore, it does not need a printer to print out the identifier (barcode) 60 and the user can easily retrieve the identifier (barcode) 60 by scanning the identifier (barcode) 60 on the monitor 50 with a CCD (charge coupled device) of a mobile device 80 such as a mobile phone or a PDA (Personal Digital Assistant) with photographing function. The identifier (barcode) 60 obtained from the mobile devices 80 is available for the user to save, manage and utilize the information. Above techniques are designed to achieve the first object of the present invention.

Most current prior arts of are equipped with measuring modules 20 to measure exercising data such as exercising duration, distance, speed, caloric consumption and total mileage, or to measure user's body condition such as pulse, heart rate, electrocardiogram and breathing capacity. In the present invention, the exercising data can be measured by a measuring element 21 (e.g., measuring revolutions per minute or torque) defined on the fitness mechanism 11. The microprocessor of the signal processing module 30 has a timer (clock) defined to measure the exercising duration as reference of other measurement to calculate above exercising data. The user's body condition can be measured by sensors 22 of pulse, heart rate, electrocardiogram or breathing capacity to generate signals for the signal processing module 30 to process the signals and save as user's physical information.

With modern level of technology, the measuring module 20 is able to measure the movement of the fitness mechanism 11 and/or the physical status of the user and to generate the fitness signals and/or the physical signals. Therefore, above technical features of the present invention are achievable.

II. The Second Embodiment of the Present Invention

Figure 3:
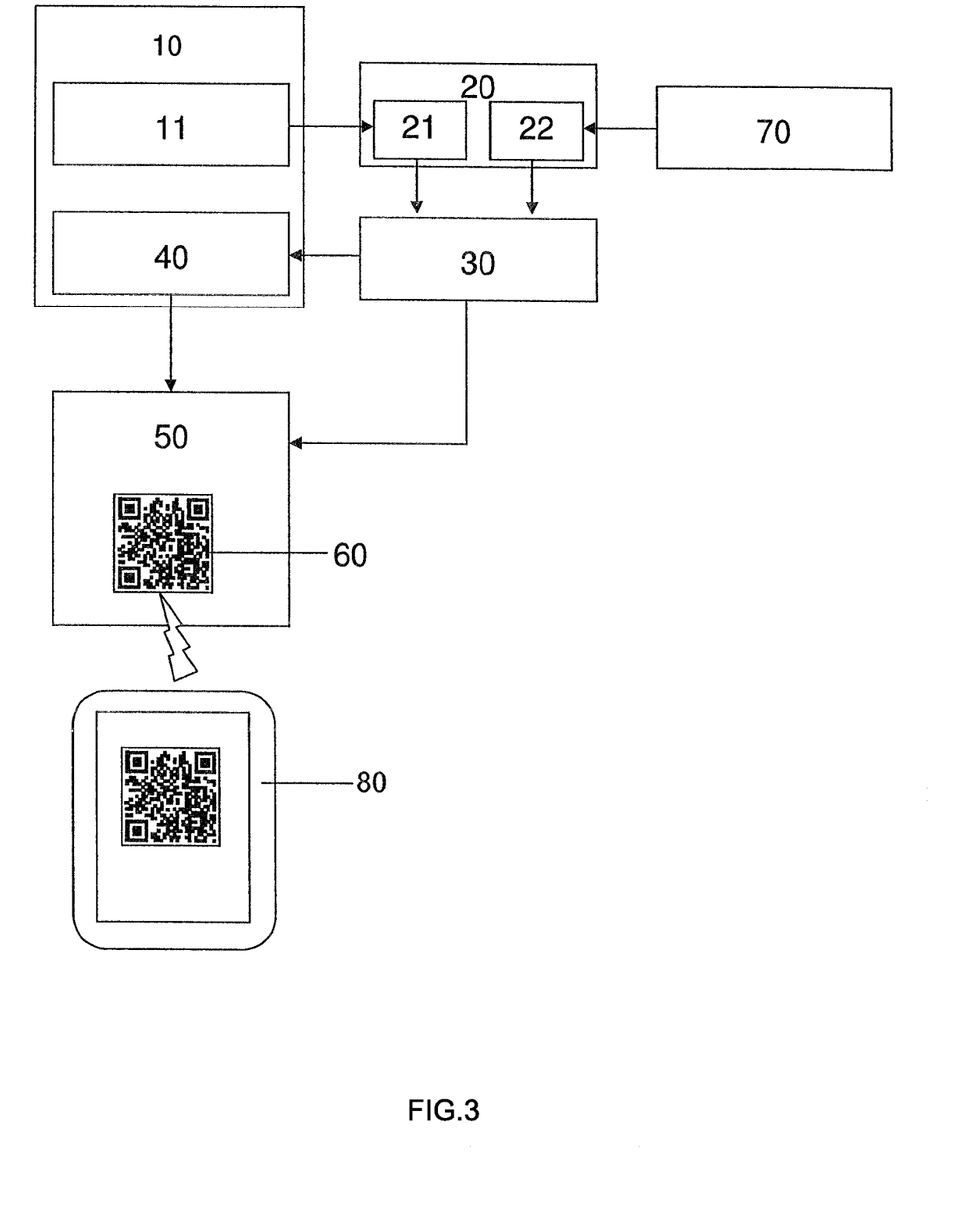
FIG. 3 is a systematic flow chart of the second embodiment in accordance with the present invention.
Figure 4:
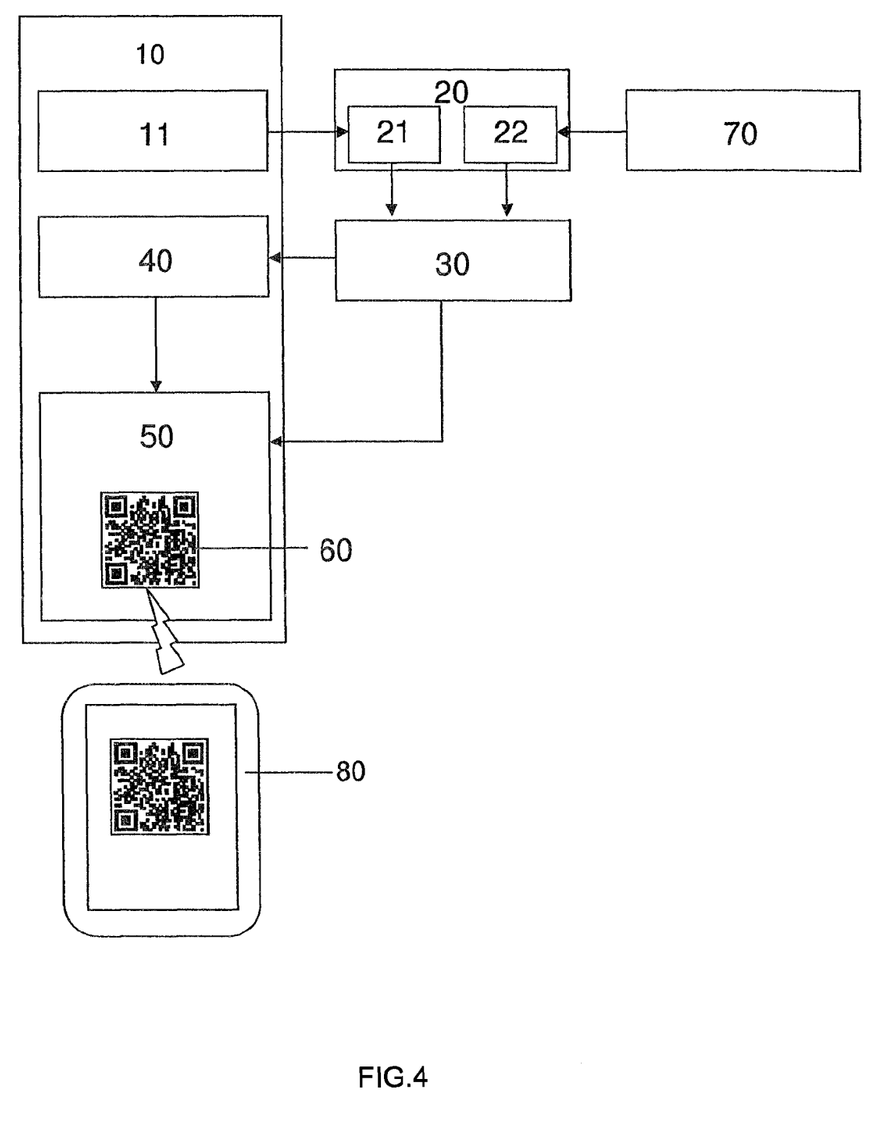
FIG. 4 is a systematic flow chart of the third embodiment in accordance with the present invention.

Referring to FIGS. 1 and 3, it is an embodiment to achieve the second object of the present invention. The system comprises a main frame 10 of the exerciser, a measuring module 20, a signal processing module 30 and an identifier generating module 40 allocated on the main frame 10. The fitness mechanism 11 of the main frame 10 allows a user 70 to do exercise and activate functions of the system. The processing steps are depicted as below. First of all, the measuring module 20 measures the movement of the fitness mechanism 11 and/or the physical status of the user and then generates fitness signals and/or physical signals. Secondly, the signal processing module 30 receives and processes the fitness signals and/or physical signals and then generates fitness information and/or physical information. The substantial embodiment of its operation is stated as the second paragraph in the first embodiment. The technical features of the present invention are achievable with modern level of technology. The identifier generating module 40 allocated on the main frame 10 retrieves and converts the fitness information and/or physical information into an identifier (barcode) 60 which will be displayed on the monitor 50. It does not need an external computer system to generate the identifier (barcode) 60 or a printer to print out the identifier (barcode) 60. Therefore, the identifier (barcode) 60 can be generated from the main frame 10 at the user end and the user can easily obtain the identifier (barcode) 60 to save, manage and utilize the information.

III. The Third Embodiment of the Present Invention

Referring to FIGS. 1, 4, 7 and 8, it is an embodiment to achieve the third object of the present invention. The system comprises a main frame 10 of the exerciser, a measuring module 20, a signal processing module 30 and an identifier generating module 40 with a monitor 50 allocated on the main frame 10. The fitness mechanism 11 of the main frame 10 allows a user 70 to do exercise and activate functions of the system. The processing steps are depicted as below. First of all, the measuring module 20 measures the movement of the fitness mechanism 11 and/or the physical status of the user and then generates fitness signals and/or physical signals. Secondly, the signal processing module 30 receives and processes the fitness signals and/or physical signals and then generates fitness information and/or physical information. The substantial embodiment of its operation is stated as the second paragraph in the first embodiment. The technical features of the present invention are achievable with modern level of technology. The identifier generating module 40 allocated on the main frame 10 retrieves and converts the fitness information and/or physical information into an identifier (barcode) 60 which will be displayed on the monitor 50. It does not need an external computer system to generate the identifier (barcode) 60 or a printer to print out the identifier (barcode) 60. Therefore, the identifier (barcode) 60 can be generated from the main frame 10 at the user end and the user can immediately obtain the identifier (barcode) 60 by using mobile devices 80 to save, manage and utilize the information.

IV. The Fourth Embodiment of the Present Invention

Figure 5:
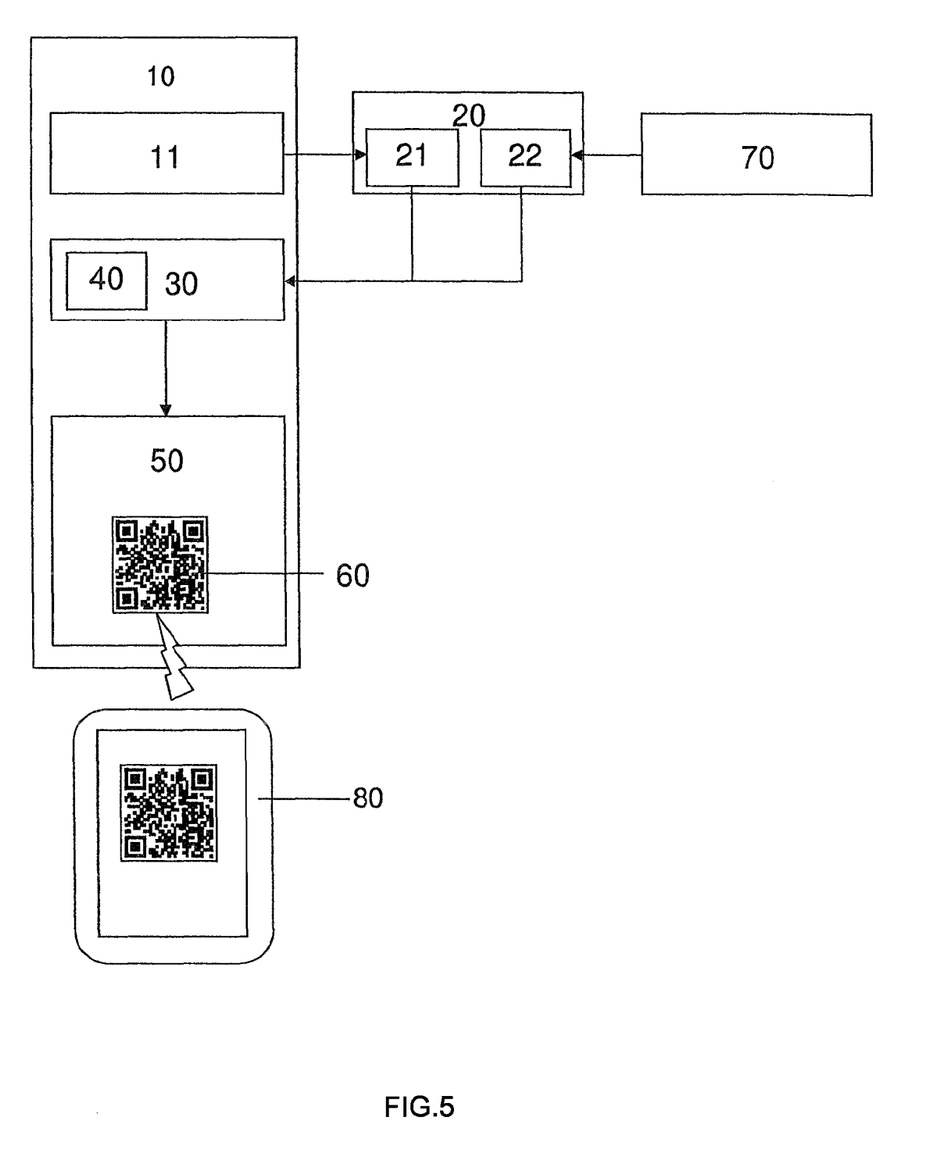
FIG. 5 is a systematic flow chart of the fourth embodiment in accordance with the present invention.

Referring to FIGS. 1 and 5, it is an embodiment to achieve the fourth object of the present invention. The system comprises a main frame 10 of the exerciser, a measuring module 20, a signal processing module 30 and an identifier generating module 40 built in the signal processing module on 30 the main frame 10. The fitness mechanism 11 of the main frame 10 allows a user 70 to do exercise and activate functions of the system. The processing steps are depicted as below. First of all, the measuring module 20 measures the movement of the fitness mechanism 11 and/or the physical status of the user and then generates fitness signals and/or physical signals. Secondly, the signal processing module 30 receives and processes the fitness signals and/or physical signals and then generates fitness information and/or physical information. The substantial embodiment of its operation is stated as the second paragraph in the first embodiment. The technical features of the present invention are achievable with modern level of technology. The identifier generating module 40, allocated on the main frame 10, directly and promptly retrieves the fitness information and/or physical information from the signal processing module 30 and converts the fitness information and/or physical information into an identifier (barcode) 60 which will be displayed on the monitor 50. It does not need an external computer system to generate the identifier (barcode) 60 or a printer to print out the identifier (barcode) 60. Therefore, the fitness information and/or physical information can be promptly and directly retrieved and the identifier (barcode) 60 can be generated and displayed from the main frame 10 at the user end for the user to conveniently obtain the identifier (barcode) 60 and to save, manage and utilize the information. Wherein, the identifier generating module 40 is a coded program to generate barcodes and is built in the signal processing module 30. It is coded in a micro-processor in the signal processing module 30. In other words, the identifier generating module 40 is integrated with the signal processing module 30 of the main frame 10.

V. The Fifth Embodiment of the Present Invention

Referring to FIGS. 1 and 2, it is an embodiment to achieve the fifth object of the present invention. The system comprises a main frame 10 of the exerciser, a measuring module 20, a signal processing module 30 and an identifier generating module 40. The fitness mechanism 11 of the main frame 10 allows a user 70 to do exercise and activate functions of the system. The measuring module 20 measures the movement of the fitness mechanism 11 and/or the physical status of the user and then generates fitness signals and/or physical signals. The processing steps are depicted as following: the signal processing module 30 receives and processes the fitness signals and/or physical signals and then generates fitness information and/or physical information. The substantial embodiment of its operation is stated as the second paragraph in the first embodiment. The technical features of the present invention are achievable with modern level of technology. The identifier generating module 40 encodes and converts the fitness information and/or physical information into a one-dimensional barcode, a two-dimensional barcode, a text code or a pattern code as the identifier 60 (a better embodiment preferring two-dimensional barcode like Quick Response Code—QR Code) to be displayed on the monitor 50. Therefore, the user can easily retrieve the identifier (barcode) 60 via videotaping or taking a picture by a mobile device without a printer. The mobile device is capable of downloading and installing editing software like APP from the Internet to process the image of the identifier 60 in the form of two-dimensional barcode, and then to generate the corresponding fitness information and/or physical information for the user to save, manage and utilize the information.

VI. The Sixth Embodiment of the Present Invention

Figure 6:
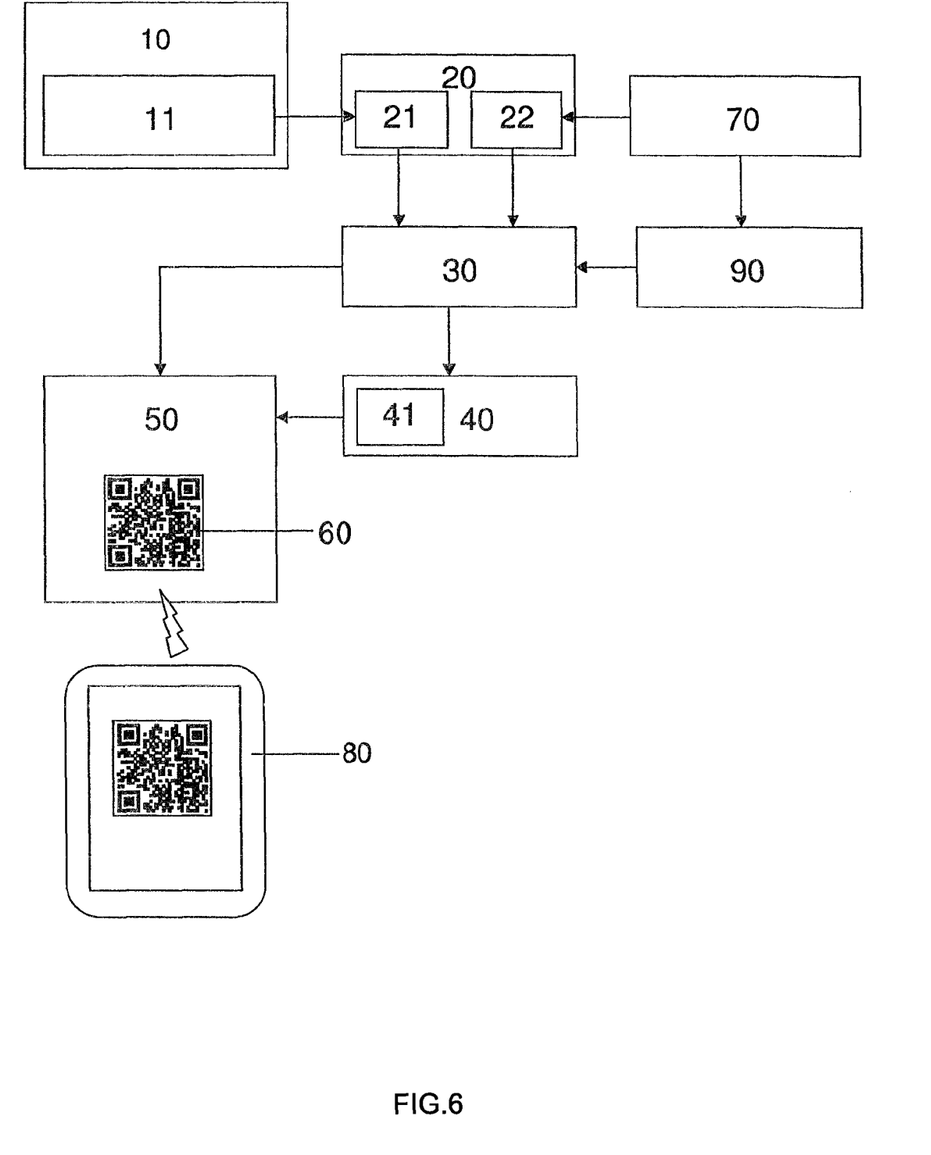
FIG. 6 is a systematic flow chart of the sixth embodiment in accordance with the present invention.

Referring to FIGS. 1 and 6, it is an embodiment to achieve the sixth object of the present invention. The system comprises a main frame 10 of the exerciser, a user's ID identifying module 90, a measuring module 20, a signal processing module 30 and an identifier generating module 40 with a built in securing module 41. The user's ID identifying module 90 receives and identifies the user's personal information and then decides proper exercise for the user to operate the fitness mechanism 11. The fitness mechanism 11 of the main frame 10 allows a user 70 to do exercise and activate functions of the system. The processing steps are depicted as below. First of all, the measuring module 20 measures the movement of the fitness mechanism 11 and/or the physical status of the user and then generates fitness signals and/or physical signals. Secondly, the signal processing module 30 receives and processes the fitness signals and/or physical signals and then generates fitness information and/or physical information. The substantial embodiment of its operation is stated as the second paragraph in the first embodiment. The technical features of the present invention are achievable with modern level of technology. The identifier generating module 40 converts the fitness information and/or physical information into an identifier (barcode) 60. The securing module 41 encodes and secures the user's personal information into the identifier (barcode) 60 which will be displayed on the monitor. It does not need a printer to print out the identifier (barcode) 60, and the user can use a mobile device to conveniently obtain the personal identifier (barcode) 60 for exclusively saving, managing and utilizing the information.

While we have shown and described the embodiment in accordance with the present invention, it should be clear to those skilled in the art that further embodiments may be made without departing from the scope of the present invention.

What is claimed is:

1. A method of information management for exercisers comprising:
    providing an exercise recipe managing module, an exercise recipe inputting module, a signal processing module, a measuring module, an identifier generating module and an exerciser including a main frame having a fitness mechanism;
    said fitness mechanism allowing a user to do exercise and activate functions of said system;
    said measuring module measuring at least one movement of said fitness mechanism and/or one physical status of said user and then generating at least one fitness signal and/or at least one physical signal;
    said signal processing module receiving and processing said at least one fitness signal and/or said at least one physical signal and then generating at least one fitness information and/or at least one physical information; and
    said identifier generating module converting said at least one fitness information and/or said at least one physical information into an identifier to be displayed on a monitor.

2. The method as claimed in claim 1, wherein, said identifier generating module is defined on said main frame, retrieves said at least one fitness information and/or said at least one physical information from said signal processing module, and then generates said identifier.

3. The method as claimed in claim 1, wherein, said identifier generating module is defined on said main frame.

4. The method as claimed in claim 1, wherein, said monitor is defined on said main frame.

5. The method as claimed in claim 1, wherein, said identifier generating module is built in said signal processing module.

6. The method as claimed in claim 1, wherein, said identifier is selected from the groups of a one-dimensional barcode, a two-dimensional barcode, a text code or a pattern code.

7. The method as claimed in claim 1, wherein, said identifier is QR Code (Quick Response Code).

8. The method as claimed in claim 1, further providing a user's ID identifying module to receive and identify said user's personal information and a securing module built in said user's ID identifying module to encode said user's personal information into said identifier.

9. The method as claimed in claim 1, wherein, said exerciser is selected from the groups of a cycling equipment, a treadmill, an elliptical equipment, a weight lifting equipment, a body-building equipment and a rehabilitation equipment.

* * * * *